(12) United States Patent
Slepnev et al.

(10) Patent No.: US 7,368,246 B2
(45) Date of Patent: May 6, 2008

(54) QUANTITATIVE GENE EXPRESSION PROFILING

(75) Inventors: Vladimir I. Slepnev, Newton, MA (US); Elizabeth Garcia, Barrington, RI (US)

(73) Assignee: Primera Biosystems, Inc., Mansfield, MA (US)

( * ) Notice: Subject to any disclaimer, the term of this patent is extended or adjusted under 35 U.S.C. 154(b) by 115 days.

(21) Appl. No.: 11/227,942

(22) Filed: Sep. 15, 2005

(65) Prior Publication Data

US 2007/0059715 A1   Mar. 15, 2007

(51) Int. Cl.
*C12Q 1/68*    (2006.01)
*C12P 19/34*   (2006.01)
(52) U.S. Cl. .......................................... 435/6; 435/91.2
(58) Field of Classification Search ...................... None
See application file for complete search history.

(56) References Cited

U.S. PATENT DOCUMENTS

| | | | |
|---|---|---|---|
| 5,213,961 | A | 5/1993 | Bunn et al. |
| 5,219,727 | A | 6/1993 | Wang et al. |
| 5,262,311 | A | 11/1993 | Pardee et al. |
| 5,580,726 | A | 12/1996 | Villeponteau et al. |
| 5,593,839 | A | 1/1997 | Hubbell et al. |
| 5,599,672 | A | 2/1997 | Liang et al. |
| 5,665,547 | A | 9/1997 | Pardee et al. |
| 5,837,832 | A | 11/1998 | Chee et al. |
| 5,856,101 | A | 1/1999 | Hubbell et al. |
| 5,994,076 | A | 11/1999 | Chenchik et al. |
| 6,045,988 | A | 4/2000 | Helling et al. |
| 6,203,989 | B1 | 3/2001 | Goldberg et al. |
| 6,271,957 | B1 | 8/2001 | Quate et al. |
| 6,287,778 | B1 | 9/2001 | Huang et al. |
| 2003/0077611 | A1 | 4/2003 | Slepnov |
| 2003/0235844 | A1 | 12/2003 | Slepnov |

FOREIGN PATENT DOCUMENTS

WO   WO 92/11273   7/1992
WO   WO 93/02215   2/1993

OTHER PUBLICATIONS

Bier, et al., "Feature-size limitations of microarray technology—a critical review", *Fresenius J Anal Chem* 371:151-156 (2001).

Borson, et al., "Direct Quantitation of RNA Transcripts by Competitive Single-Tube RT-PCR and Capillary Electrophoresis", *Biotechniques* 25:130-137 (1998).
Chelly, et al., "Transcript of the dystrophin gene in human muscle and non-muscle tissues", *Nature* vol. (Jun. 30, 1988), 333:858.
Dhiman, et al., "Gene expression microarrays: a 21st century tool for directed vaccine design", *Vaccine* 20:22-30 (2002).
George, et al., "Capillary electrophoresis methodology for identification of cancer related gene expression patterns of fluorescent differential display polymerase chain reaction", *Journal of Chromatography B* 695:93-102 (1997).
Greenberg, "DNA microarray gene expression analysis technology and its application to neurological disorders", *Neurology* 57:755-761 (2001).
Kievits, et al., "NASBA™ isothermal enzymatic in vitro nucleic acid amplification optimized for the diagnosis of HIV-1 infection", *Journal of Virological Methods*, 35:273-286 (1991).
Liang, et al., "Differential Display, A General Protocol", *Molecular Biotechnology* 1073-6085/10:3/261-267 (1998).
Luehrsen, et al., *Biotechniques* 22:168-174 (Jan. 1997).
Merlino, et al., "Polyomavirus BK DNA quantification assay to evaluate viral load in renal transplant recipients", *Journal of Clinical Virology* 28:265-274 (2003).
Mills, et al., "DNA microarrays and beyond: completing the journeys from tissue to cell", *Nature Cell Biology* 3:E175-178 (2001).
Odin, et al., "Rapid method for relative gene expression determination in human tissues using automated capillary gel electrophoresis and multicolor detection", *Journal of Chromatography B* 734:47-53 (1999).
Omori, et al., "Comparative PCR: A Simple and Sensitive Method for Quantifying Low-Abundance mRNA Species", *Genomics* 67:140-145 (2000).
Rajĉeviĉ, et al., "Assessment of differential expression of oncogenes in gastric adenocarcinoma by fluorescent multiplex RT-PCR assay", *Pflugers Arch.* 442 (Suppl 1):R190-192 (2001).
Walker, "Multiplex strand displacement amplification (SDA) and detection of DNA sequences from *Mycobacterium tuberculosis* and other mycobacteria", *Nucleic Acids Research* 2670-2677, 22:13 (1994).
Wu, "Analysing gene expression data from DNA microarrays to identify candidate genes", *Journal of Pathology* 195:53-65 (2001).

*Primary Examiner*—James Martinell
(74) *Attorney, Agent, or Firm*—Mark J. FitzGerald; Nixon Peabody LLP (57) ABSTRACT

Described herein are approaches to the measurement of gene expression for chosen genes in a biological sample. The methods permit the quantitation of target nucleic acids, e.g., DNAs or RNAs in a nucleic acid sample, both singly and in a multiplex format that permits the determination of levels (e.g., expression levels or copy numbers) for two or more target nucleic acids in a single reaction.

25 Claims, 1 Drawing Sheet

Figure 1. Schematic of one embodiment of a quantitative gene expression profiling method as described.

QUANTITATIVE GENE EXPRESSION PROFILING

FIELD OF THE INVENTION

The invention relates to methods and compositions for the measurement of nucleic acids. More particularly, the invention relates to methods and compositions for measuring levels of DNA and/or RNA in biological samples.

BACKGROUND OF THE INVENTION

The introduction of genomics has been instrumental in accelerating the pace of drug discovery. The genomic technologies have proved their value in finding novel drug targets. Further improvement in this area will provide more efficient tools resulting in faster and more cost efficient development of potential drugs.

The drug discovery process includes several steps: the identification of a potential biochemical target associated with disease, screening for active compounds and further chemical design, preclinical tests, and finally clinical trials. The efficiency of this process is still far from perfect: it is estimated that about 75% of money spent in the R&D process went to fund failed projects. Moreover, the later in the product development a failure occurs, the bigger are losses associated with this project. Thus it is important to eliminate early in the process future failures in order to reduce costs of the whole drug development process. Thus, the quality of the original molecular target becomes a decisive factor for cost-effective drug development.

One approach that promises to impact on the process of target identification and validation is transcription profiling. This method compares expression of genes in a specific situation: for example, between disease and normal cells, between control and drug-treated cells or between cells responding to treatment and those resistant to it. The information generated by this approach can directly identify specific genes to be targeted by a therapy, and, importantly, reveals biochemical pathways involved in disease and treatment. In brief, it not only provides biochemical targets, but at the same time, a way to assess the quality of these targets. Moreover, in combination with cell-based screening, transcription profiling is positioned to dramatically change the field of drug discovery. Historically, screening for a potential drug was successfully performed using phenotypic change as a marker in functional cellular system. For example, growth of tumor cells in culture was monitored to identify anticancer drugs. Similarly, bacterial viability was used in assays aimed at identifying antibiotic compounds. Such screens were typically conducted without prior knowledge of the targeted biochemical pathway. In fact, the identified effective compounds often revealed such pathways and pointed out the true molecular target, enabling subsequent rational design of the next generations of drugs.

Modern tools of transcription profiling can be used to design novel screening methods that will utilize gene expression in place of phenotypic changes to assess effectiveness of a drug. For example, some methods are described in U.S. Pat. Nos. 5,262,311; 5,665,547; 5,599,672; 5,580,726; 6,045,988 and 5,994,076, as well as Luehrsen et al. (1997, Biotechniques, 22:168-74; Liang and Pardee (1998, Mol Biotechnol. 10:261-7). Such approaches will be invaluable, for example, for drug discovery in the field of central nervous system (CNS) disorders such as dementia, mild cognitive impairment, depression, etc., where phenotypic screening is inapplicable, but where a transcription profile can be established and linked to particular disorders. Once again, the identified effective compounds will likely reveal the underlying molecular processes. This approach can also be instrumental for the development of improved versions of existent drugs, which act at several biochemical targets at the same time to generate a desired pharmacological effect. In such case the change in the transcriptional response may be a better marker for drug action than selection based on optimization of binding to multiple targets.

In addition to uses in drug development, transcriptional profiling and other measurements of nucleic acid presence or abundance can be used for diagnosis, for example, where expression, overexpression or lack of expression of a particular gene or set of genes correlates with a given disease state or predisposition. Similarly, where copy number (amplification, deletion or disruption) of a gene sequence at the chromosomal level correlates with a disease or disease predisposition, determination of DNA copy number in an individual or in a tissue or cell type can predict or diagnose that disease.

Common methods of transcription profiling are based on technology using DNA microarrays, for example, as reviewed in Greenberg, 2001 Neurology 57:755-61; Wu, 2001, J Pathol. 195:53-65; Dhiman et al., 2001, Vaccine 20:22-30; Bier et al., 2001 Fresenius J Anal Chem. 371: 151-6; Mills et al., 2001, Nat Cell Biol. 3:E175-8; and as described in U.S. Pat. Nos. 5,593,839; 5,837,832; 5,856,101; 6,203,989; 6,271,957; and 6,287,778. The DNA microarray approach performs simultaneous comparison of the expression of several thousand genes in a given sample by assessing hybridization of the labeled polynucleotide samples, obtained by reverse transcription of mRNAs, to the DNA molecules attached to the surface of the test array.

The microarray approach screens the pool of genes presented in the microarray. The current printing methods allows placement of 10,000-15,000 genes on a single chip, which is essentially a number of genes expressed in a particular cell type. Given the diversity of cell types, it requires development of specific arrays for specific cell types. Microarrays tend to provide qualitative, rather than quantitative results.

The number of transcripts in a tissue sample is even higher than in a cellular sample and can exceed the capacity of a microarray.

Exogenous control involves the use of an artificially introduced nucleic acid molecule that is added, either to the extraction step or to the PCR step, in a known concentration. The concept of adding an exogenous nucleic acid at a known concentration in order to act as an internal standard for quantitation was introduced by Chelly et al. (1988) Nature 333: 858-860, which is specifically incorporated herein by reference. Therefore, utilizing a control fragment that is amplified with the same primers as the target sequence more accurately reflects target sequence amplification efficiency relative to the internal standard (see, for example, WO 93/02215; WO 92/11273.; U.S. Pat. Nos. 5,213,961 and 5,219,727, all of which are incorporated herein by reference). Similar strategies have proven effective for quantitative measurement of nucleic acids utilizing isothermal amplification reactions such as NASBA (Kievits et al., 1991, J. Virol. Methods 35: 273-86) or SDA (Walker, 1994, Nucleic Acids Res. 22: 2670-7).

Capillary electrophoresis has been used to quantitatively detect gene expression. Rajevic at el. (2001, Pflugers Arch. 442(6 Suppl 1):R190-2) discloses a method for detecting differential expression of oncogenes by using seven pairs of primers for detecting the differences in expression of a number of oncogenes simultaneously. Sense primers were 5' end-labelled with a fluorescent dye. Multiplex fluorescent RT-PCR results were analyzed by capillary electrophoresis on ABI-PRISM 310 Genetic Analyzer. Borson et al. (1998, Biotechniques 25:130-7) describes a strategy for dependable quantitation of low-abundance mRNA transcripts based on quantitative competitive reverse transcription PCR (QC-RT-PCR) coupled to capillary electrophoresis (CE) for rapid separation and detection of products. George et al., (1997, J Chromatogr B BIOMED Sci Appl 695:93-102) describes the application of a capillary electrophoresis system (ABI 310) to the identification of fluorescent differential display generated EST patterns. Odin et al. (1999, J Chromatogr B Biomed Sci Appl 734:47-53) describes an automated capillary gel electrophoresis with multicolor detection for separation and quantification of PCR-amplified cDNA.

Omori et al. (2000, Genomics 67:140-5) measures and compares the amount of commercially purchased α-globin mRNA by competitive PCR in two independently reverse transcribed cDNA samples using oligo(dT) or oligo(dU) primers. The oligo(dT) or oligo(dU) primers share a 3' oligo(dT) or oligo(dU) sequence and a 5' common sequence. In addition the oligo(dT) or oligo(dU) primer for each sample also contains a unique 29 nucleotide sequence between the 3' oligo(dT) or oligo(dU) sequence and the 5' common sequence. After the synthesis of first strand cDNA, PCR is performed to amplify the cDNA using a gene-specific primer and a primer complementary to the common sequence which is labeled with a unique label. The amplified PCR products are then analyzed by spotting onto a detection plate of a fluorescence scanner.

SUMMARY OF THE INVENTION

Disclosed herein are methods for determining the amount of one or a number of target polynucleotides, e.g., DNAs or RNAs, in a given biological sample. The methods described herein permit the determination of, for example, gene expression levels of one or more target gene sequences, in a high throughput manner suited to the development and comparison of gene expression profiles in biological samples. Gene expression profiles may be thought of as a snapshot of the expression state of a set of target genes in, for example, a given tissue or organism. The comparison of gene expression profiles can provide valuable information, for example, with regard to mechanisms of disease and the activity of known or potential drug candidates.

In one aspect, the invention relates to methods of estimating or determining the level of a target nucleic acid, e.g., a DNA or RNA in a nucleic acid sample, the method comprising: for a given target nucleic acid, selecting a pair of amplification primers that will generate a target amplicon of known length upon amplification of the target, e.g., by PCR or RT-PCR. A set of at least two competitor nucleic acids (e.g., DNA or RNA molecules) is generated, where the competitors yield products of differing lengths but similar amplification efficiencies relative to the target nucleic acid when amplified using the same pair of amplification primers. An amplification reaction is performed in which a sample to be analyzed for target nucleic acid level is mixed with known and differing concentrations of the at least two competitor nucleic acids, followed by separation and detection of the amplified products. The set of competitor nucleic acids provides an internal reference for the determination of target nucleic acid amount in the original sample. This approach is readily adapted to measure multiple target nucleic acids in a single sample in a single run, which permits the generation of an amplification profile for the selected target gene sequences in a given sample.

DEFINITIONS

As used herein, the term "amplicon" refers to an amplification product from a nucleic acid amplification reaction. The term generally refers to an anticipated, specific amplification product of known size, generated using a given set of amplification primers.

As used herein, the term "reverse transcript" refers to a DNA complement of an RNA strand generated by an RNA-dependent DNA polymerase activity.

As used herein, the term "competitor nucleic acid" or "nucleic acid competitor" refers to a nucleic acid template of known length and composition which can be amplified using a pair of oligonucleotide primers selected for the amplification of a target nucleic acid. In certain embodiments, the competitor nucleic acid can be an RNA molecule, in which case it can be referred to as a "competitor RNA" or an "RNA competitor." In other embodiments, the competitor nucleic acid can be a DNA molecule, in which case it can be referred to as a "competitor DNA" or a "DNA competitor." A "competitor nucleic acid" (whether DNA or RNA) is longer or shorter than the target nucleic acid, e.g., by a known, distinguishable length, e.g., the length of an internal insertion or deletion in the target nucleic acid, respectively. The internal insertion or deletion should be from 1 to 20 nucleotides or bases, preferably 5 to 20 nucleotides or bases, or 5 to 10 nucleotides or bases. The difference in length of the target and competitior amplicons will be from 1 to 20 nucleotides in length, preferably 5 to 20 or 5 to 10 nucleotides in lenthg. Inserted sequence will preferably not introduce the capacity for stable secondary structure not present in the target sequence. Software for predicting nucleic acid secondary structure is well known in the art. A "competitor nucleic acid" will have an amplification efficiency that is similar to that of the target nucleic acid when using a selected pair of amplification primers.

As used herein, the term "similar efficiency" when applied to nucleic acid amplification, means that the threshold cycle (Ct) for the detection of target and competitor nucleic acid amplification products generated using the same set of primers and equal amounts of target and competitor template is the same. It is possible to calculate Ct to a fraction of a cycle. However, the Ct for one amplicon is "the same" as the Ct for another amplicon when the whole cycle numbers are the same—i.e., Ct's of 2.0, 2.3 and 2.6 are "the same" as the term is used herein. As used herein, "Ct" is the PCR cycle at which at which signal intensity of PCR product reaches a threshold value of 10 standard deviations of background value of signal intensity for an amplified product. Signal intensity in this context refers to fluorescent signal from amplification product incorporating fluorescent label (either by labeled primer or labeled nucleotide incorporation), measured following capillary electrophoresis of amplified products present in samples withdrawn from a cycling reaction at a plurality of cycle points. Another measure of amplication efficiency is to measure the amount of amplification product (e.g., by fluorescense integrity or lable incorporation) at successive cycles, calculating efficiency using the formula $E=(P_{n+1}-P_n)/(P_n-P_{n-1})$, where P=the amount of amplification product at cycle n. Amplification efficiency is "similar" if the difference in efficiency between target and competitor nucleic acid is less than 0.2 in absolute value.

In the methods described herein, efficiency is "similar" if the efficiency of amplification of target and competitor nucleic acid is "similar" by either of these criteria, and preferably, by both.

As used herein, reference to "separating" or the "separation of" nucleic acids in a sample refers to a method of nucleic acid separation capable of resolving nucleic acid fragments that differ in size by 10 bases or less (or, alternatively, by 10 base pairs or less, e.g., where non-denaturing conditions are employed). Preferred resolution for separation techniques employed in the methods described herein includes resolution of nucleic acids differing by 5 nucleotides or less (alternatively, 5 base pairs or less), up to and including resolution of nucleic acids differing by only one nucleotide (or one base pair).

As used herein, reference to a "size distinguishable by capillary electrophoresis" means a difference of at least one nucleotide (or base pair), but preferably at least 5 nucleotides (or base pairs) or more, up to and including 10 nucleotides (or base pairs) or more.

As used herein, the term "sample" refers to a biological material which is isolated from its natural environment and contains a polynucleotide. A "sample" according to the invention may be tissue or cell extract or it may contain purified or isolated polynucleotide.

As used herein, the term "amplified product" refers to polynucleotides which are copies of a particular polynucleotide, produced in an amplification reaction. An "amplified product," according to the invention, may be DNA or RNA, and it may be double-stranded or single-stranded.

As used herein, the term "amplification" or "amplification reaction" refers to a reaction for generating a copy of a particular polynucleotide sequence or increasing the copy number or amount of a particular polynucleotide sequence. For example, polynucleotide amplification may be a process using a polymerase and a pair of oligonucleotide primers for producing any particular polynucleotide sequence, i.e., the whole or a portion of a target polynucleotide sequence, in an amount which is greater than that initially present. Amplification may be accomplished by the in vitro methods of the polymerase chain reaction (PCR). See generally, PCR Technology: Principles and Applications for DNA Amplification (H. A. Erlich, Ed.) Freeman Press, NY, N.Y. (1992); PCR Protocols: A Guide to Methods and Applications (Innis et al., Eds.) Academic Press, San Diego, Calif. (1990); Mattila et al., Nucleic Acids Res. 19: 4967 (1991); Eckert et al., PCR Methods and Applications 1: 17 (1991); PCR (McPherson et al. Ed.), IRL Press, Oxford; and U.S. Pat. Nos. 4,683,202 and 4,683,195, each of which is incorporated by reference in its entirety. Other amplification methods include, but are not limited to: (a) ligase chain reaction (LCR) (see Wu and Wallace, Genomies 4: 560 (1989) and Landegren et al., Science 241: 1077 (1988)); (b) transcription amplification (Kwoh et al., Proc. Natl. Acad. Sci. USA 86: 1173 (1989)); (c) self-sustained sequence replication (Guatelli et al., Proc. Natl. Acad. Sci. USA, 87: 1874 (1990)); and (d) nucleic acid based sequence amplification (NABSA) (see, Sooknanan, R. and Malek, L., Bio Technology 13: 563-65 (1995)), each of which is incorporated by reference in its entirety.

As used herein, the term "aliquot" refers to a sample volume taken from an amplification reaction mixture. The volume of an aliquot can vary, but will generally be constant within a given experimental run. An aliquot will be less than the volume of the entire reaction mixture. Where there are X aliquots to be withdrawn during an amplification regimen, the volume of an aliquot will be less than or equal to 1/X times the reaction volume.

As used herein, the term "dispense" means dispense, transfer, withdraw, extrude or remove.

As used herein, the phrase "dispensing an aliquot from the reaction mixture at plural stages" refers to the withdrawal of an aliquot at least twice, and preferably at least 3, 4, 5, 10, 15, 20, 30 or more times during an amplification reaction. A "stage" will refer to a point at or after a given number of cycles, or, where the amplification regimen is non-cyclic, will refer to a selected time at or after the initiation of the reaction.

As used herein, a "target polynucleotide" (including, e.g., a target RNA or target DNA) is a polynucleotide to be analyzed. A target polynucleotide may be isolated or amplified before being analyzed using methods of the present invention. For example, the target polynucleotide may be a sequence that lies between the hybridization regions of two members of a pair of oligonucleotide primers which are used to amplify it. A target polynucleotide may be RNA or DNA (including, e.g., cDNA). A target polynucleotide sequence generally exists as part of a larger "template" sequence; however, in some cases, a target sequence and the template are the same.

As used herein, an "oligonucleotide primer" refers to a polynucleotide molecule (i.e., DNA or RNA) capable of annealing to a polynucleotide template and providing a 3' end to produce an extension product which is complementary to the polynucleotide template. The conditions for initiation and extension usually include the presence of four different deoxyribonucleoside triphosphates (dNTPs) and a polymerization-inducing agent such as a DNA polymerase or reverse transcriptase activity, in a suitable buffer ("buffer" includes substituents which are cofactors, or which affect pH, ionic strength, etc.) and at a suitable temperature. The primer as described herein may be single- or double-stranded. The primer is preferably single-stranded for maximum efficiency in amplification. "Primers" useful in the methods described herein are less than or equal to 100 nucleotides in length, e.g., less than or equal to 90, or 80, or 70, or 60, or 50, or 40, or 30, or 20, or 15, but preferably longer than 10 nucleotides in length.

As used herein, "label" or "detectable label" refers to any moiety or molecule which can be used to provide a detectable (preferably quantifiable) signal. A "labeled nucleotide" (e.g., a dNTP), or "labeled polynucleotide", is one linked to a detectable label. The term "linked" encompasses covalently and non-covalently bonded, e.g., by hydrogen, ionic, or Van der Waals bonds. Such bonds may be formed between at least two of the same or different atoms or ions as a result of redistribution of electron densities of those atoms or ions. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A nucleotide useful in the methods described herein can be labeled so that the amplified product may incorporate the labeled nucleotide and becomes detectable. A fluorescent dye is a preferred label according to the present invention. Suitable fluorescent dyes include fluorochromes such as Cy5, Cy3, rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane (see for example, DeLuca, *Immunofluorescence Analysis*, in

*Antibody As a Tool*, Marchalonis, et al., eds., John Wiley & Sons, Ltd., (1982), which is incorporated herein by reference).

It is intended that the term "labeled nucleotide", as used herein, also encompasses a synthetic or biochemically derived nucleotide analog that is intrinsically fluorescent, e.g., as described in U.S. Pat. Nos. 6,268,132 and 5,763,167, Hawkins et al. (1995, Nucleic Acids Research, 23: 2872-2880), Seela et al. (2000, Helvetica Chimica Acta, 83: 910-927), Wierzchowski et al. (1996, Biochimica et Biophysica Acta, 1290: 9-17), Virta et al. (2003, Nucleosides, Nucleotides & Nucleic Acids, 22: 85-98), the entirety of each is hereby incorporated by reference. By "intrinsically fluorescent", it is meant that the nucleotide analog is spectrally unique and distinct from the commonly occurring conventional nucleosides in their capacities for selective excitation and emission under physiological conditions. For the intrinsically fluorescent nucleotides, the fluorescence typically occurs at wavelengths in the near ultraviolet through the visible wavelengths. Preferably, fluorescence will occur at wavelengths between 250 nm and 700 nm and most preferably in the visible wavelengths between 250 nm and 500 nm.

The term "detectable label" or "label" include a molecule or moiety capable of generating a detectable signal, either by itself or through the interaction with another label. The "label" may be a member of a signal generating system, and thus can generate a detectable signal in context with other members of the signal generating system, e.g., a biotin-avidin signal generation system, or a donor-acceptor pair for fluorescent resonance energy transfer (FRET) (Stryer et al., 1978, Ann. Rev. Biochem., 47:819; Selvin, 1995, Methods Enzymol., 246:300).

The term "nucleotide," as used herein, refers to a phosphate ester of a nucleoside, e.g., mono, di, tri, and tetra-phosphate esters, wherein the most common site of esterification is the hydroxyl group attached to the C-5 position of the pentose (or equivalent position of a non-pentose "sugar moiety"). The term "nucleotide" includes both a conventional nucleotide and a non-conventional nucleotide which includes, but is not limited to, phosphorothioate, phosphite, ring atom modified derivatives, and the like, e.g., an intrinsically fluorescent nucleotide.

As used herein, the term "conventional nucleotide" refers to one of the "naturally occurring" deoxynucleotides (dNTPs), including dATP, dTTP, dCTP, dGTP, dUTP, and dITP.

As used herein, the term "non-conventional nucleotide" refers to a nucleotide which is not a naturally occurring nucleotide. The term "naturally occurring" refers to a nucleotide that exists in nature without human intervention. In contradistinction, the term "non-conventional nucleotide" refers to a nucleotide that exists only with human intervention. A "non-conventional nucleotide" may include a nucleotide in which the pentose sugar and/or one or more of the phosphate esters is replaced with a respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide may show a preference of base pairing with another artificial nucleotide over a conventional nucleotide (e.g., as described in Ohtsuki et al. 2001, Proc. Natl. Acad. Sci., 98: 4922-4925, hereby incorporated by reference). The base pairing ability may be measured by the T7 transcription assay as described in Ohtsuki et al. (supra). Other non-limiting examples of "artificial nucleotides" may be found in Lutz et al. (1998) Bioorg. Med. Chem. Lett., 8: 1149-1152); Voegel and Benner (1996) Helv. Chim. Acta 76, 1863-1880; Horlacher et al. (1995) Proc. Natl. Acad. Sci., 92: 6329-6333; Switzer et al. (1993), Biochemistry 32: 10489-10496; Tor and Dervan (1993) J. Am. Chem. Soc. 115: 4461-4467; Piccirilli et al. (1991) Biochemistry 30: 10350-10356; Switzer et al. (1989) J. Am. Chem. Soc. 111: 8322-8323, all of which hereby incorporated by reference. An "non-conventional nucleotide" may also be a degenerate nucleotide or an intrinsically fluorescent nucleotide.

As used herein, the term "degenerate nucleotide" denotes a nucleotide which may be any of dA, dG, dC, and dT; or may be able to base-pair with at least two bases of dA, dG, dC, and dT. An unlimiting list of degenerate nucleotide which base-pairs with at least two bases of dA, dG, dC, and dT include: Inosine, 5-nitropyrole, 5-nitroindole, hypoxanthine, 6H,8H,4-dihydropyrimido[4,5c][1,2]oxacin-7-one (P), 2-amino-6-methoxyaminopurine, dPTP and 8-oxo-dGTP.

As used herein, the term "opposite orientation", when referring to primers, means that one primer comprises a nucleotide sequence complementary to the sense strand of a target polynucleotide template, and another primer comprises a nucleotide sequence complementary to the antisense strand of the same target polynucleotide template. Primers with an opposite orientation may generate a PCR amplified product from matched polynucleotide template to which they complement. Two primers with opposite orientation may be referred to as a reverse primer and a forward primer.

As used herein, the term "same orientation", means that primers comprise nucleotide sequences complementary to the same strand of a target polynucleotide template. Primers with same orientation will not generate a PCR amplified product from matched polynucleotide template to which they complement.

As used herein, a "polynucleotide" generally refers to any polyribonucleotide or poly-deoxyribonucleotide, which may be unmodified RNA or DNA or modified RNA or DNA. "Polynucleotides" include, without limitation, single- and double-stranded polynucleotides. The term "polynucleotides" as it is used herein embraces chemically, enzymatically or metabolically modified forms of polynucleotides, as well as the chemical forms of DNA and RNA characteristic of viruses and cells, including for example, simple and complex cells. A polynucleotide useful for the present invention may be an isolated or purified polynucleotide or it may be an amplified polynucleotide in an amplification reaction.

As used herein, "isolated" or "purified" when used in reference to a polynucleotide means that a naturally occurring sequence has been removed from its normal cellular environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95%, up to 99-100% pure) of non-nucleotide or polynucleotide material naturally associated with it.

As used herein, the term "cDNA" refers to complementary or copy polynucleotide produced from an RNA template by the action of RNA-dependent DNA polymerase activity (e.g., reverse transcriptase).

As used herein, "complementary" refers to the ability of a single strand of a polynucleotide (or portion thereof) to hybridize to an anti-parallel polynucleotide strand (or portion thereof) by contiguous base-pairing between the nucleotides (that is not interrupted by any unpaired nucleotides) of the anti-parallel polynucleotide single strands, thereby forming a double-stranded polynucleotide between the complementary strands. A first polynucleotide is said to be "completely complementary" to a second polynucleotide strand if each and every nucleotide of the first polynucleotide forms base-paring with nucleotides within the complementary region of the second polynucleotide. A first polynucleotide is not completely complementary (i.e., partially complementary) to the second polynucleotide if one nucleotide in the first polynucleotide does not base pair with the corresponding nucleotide in the second polynucleotide. The degree of complementarity between polynucleotide strands has significant effects on the efficiency and strength of annealing or hybridization between polynucleotide strands. This is of particular importance in amplification reactions, which depend upon binding between polynucleotide strands.

An oligonucleotide primer is "complementary" to a target polynucleotide if at least 50% (preferably, 60%, more preferably 70%, 80%, still more preferably 90% or more) nucleotides of the primer form base-pairs with nucleotides on the target polynucleotide.

As used herein, the term "analyzing," when used in the context of an amplification reaction, refers to a qualitative (i.e., presence or absence, size detection, or identity etc.) or quantitative (i.e., amount) determination of a target polynucleotide, which may be visual or automated assessments based upon the magnitude (strength) or number of signals generated by the label. The "amount" (e.g., measured in µg, µmol or copy number) of a polynucleotide may be measured by methods well known in the art (e.g., by UV absorption, by comparing band intensity on a gel with a reference of known length and amount), for example, as described in *Basic Methods in Molecular Biology*, (1986, Davis et al., Elsevier, N.Y.); and *Current Protocols in Molecular Biology* (1997, Ausubel et al., John Weley & Sons, Inc.). One way of measuring the amount of a polynucleotide in the present invention is to measure the fluorescence intensity emitted by such polynucleotide, and compare it with the fluorescence intensity emitted by a reference polynucleotide, i.e., a polynucleotide with a known amount.

The practice of the methods described herein will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Polynucleotide Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). The practice of the present invention may also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456; 5,246,577; 5,126,025; 5,364,521; 4,985,129; as well as in U.S. patent application Ser. Nos. 10/113,034; 10/387,286; 10/719,185; 10/600,201; 10/752,123 and 10/719,746. All patents, patent applications, and publications mentioned herein, both supra and infra, are hereby incorporated by reference.

DESCRIPTION

Described herein are approaches to the measurement of gene expression for chosen genes in a biological sample. The methods permit the quantitation of target nucleic acids, e.g., DNAs or RNAs in a nucleic acid sample, both singly and in a multiplex format that permits the determination of levels (e.g., expression levels or copy numbers) for two or more target nucleic acids in a single reaction.

The methods described herein use internal standards generated through the use of known differing concentrations of exogenously added competitor nucleic acids that generate amplification products of known sizes that differ from each other and from the size of the target nucleic acid(s). Size separation by, for example, capillary electrophoresis, coupled with detection by, for example, fluorescence detection, generates a standard curve from the abundance of the amplification products corresponding to the competitor nucleic acids. The standard curve permits the determination of the target nucleic acid concentration(s) in the original sample.

In one aspect, then, there is described a method of estimating the level of a target nucleic acid in a nucleic acid sample. That method comprises the following steps. First, for a given target nucleic acid, a pair of amplification primers is selected that will generate a target amplicon of a known length following reverse-transcription (for RNA target) and amplification (e.g., PCR amplification, for both RNA and DNA targets) using that pair of primers. Considerations for primer design are well known to those of skill in the art; however, among the more critical aspects are specificity, i.e., the primers chosen should amplify only the desired target molecule under at least one set of amplification conditions, and compatibility with additional primers that may be employed in a reaction, e.g., where multiplex analyses are to be performed. The length and nucleotide content (e.g., the G+C content) of the oligonucleotide primer is instrumental in determining the specificity and hybridization characteristics (e.g., melting temperature) of the primer. Further considerations for oligonucleotide primer selection or design are known to those of skill in the art and/or described herein below.

Next, a set of at least two competitor nucleic acids is created. The competitor nucleic acids share the same primer binding sequences (or their complements) for the selected amplification primers as the target nucleic acid, but differ in the length of the amplicon that will be generated using the same set of amplification primers used to amplify the target sequence. It is important that the at least two competitor nucleic acids have similar amplification efficiencies (as the term is defined herein) relative to each other and to the target nucleic acids when the selected pair of amplification primers is used to generate an amplification product from each. In the set of at least two competitor nucleic acids, it is preferred that one competitor generates a longer amplicon using the same primers, and another generates a shorter amplicon. (As discussed herein below, additional longer or shorter competitors can also be included in differing amounts, e.g., to modify the resolution of the assay.) In other embodiments, each of the at least two competitor nucleic acids can generate a longer amplicon than that generated from the target nucleic acid. It should be understood that in this instance, each of the competitors should generate amplicons of differing known lengths relative to each other and to the target amplicon. In other embodiments, each of the at least two competitor nucleic acids can generate a shorter amplicon than that generated from the target nucleic acid—here again, the competitor amplicons must differ by known lengths from each other and from the target amplicon. Methods of generating nucleic acids for use in the methods described herein are well known in the art, e.g., PCR (for DNA competitors) or in vitro transcription from plasmid or other isolated template DNA (for RNA competitors), or chemical synthesis. Methods for PCR, in vitro transcription and for the generation of templates that differ in length from a given DNA template are well known to those of skill in the art and/or described herein below.

The difference in size of the competitor nucleic acid amplicons should be a difference that can be detected by a method capable of distinguishing nucleic acids differing in size by 10 nucleotides/base pairs or less, and preferably by 5 nucleotides/base pairs or less, or even by as little as 1 nucleotide or base pair. A well-suited method is, for example, capillary electrophoresis. Conditions under which capillary electrophoresis permits the detection of length differences of as little as one nucleotide are well known. While differences of as little as one nucleotide are intended to be encompassed within the methods described herein, it is preferable that the difference between competitors and target be at least 5 nucleotides, in order to better resolve the resulting amplicons from the target amplicon upon separation by, for example, capillary electrophoresis. Differences greater than 5 nucleotides are also contemplated, e.g., 10, 20, 30, 40 or 50 nucleotides. However, the difference should not be so great as to render the efficiency of amplification significantly different (i.e., resulting in a difference in amplification efficiency E of greater than 0.2 in absolute value, where $E=(P_{n+1}-P_n)/(P_n-P_{n-1})$ (where $P_n$ is the amount of PCR product at cycle n) with respect to the efficiency of the target amplicon or the at least one other competitor amplicon(s). Factors affecting the efficiency of amplification are well known to those of skill in the art and include, for example, $T_m$ of the primers, the length of the amplicon, nucleotide composition of the amplicon, potential for secondary structure in the target or in the primers, and the presence of, for example, modified nucleotides in the reaction. The measurement of amplification efficiency and factors affecting it are known to those of skill in the art and/or described herein below.

One straightforward approach to generating competitor nucleic acids involves the internal insertion or deletion of sequences from the sequence of the target amplicon. This approach maximizes the similarities between the competitor nucleic acids and the target nucleic acids, which in turn makes it more likely that amplification efficiencies will be similar. Thus, one would perform site-directed mutagenesis on a cloned or amplified copy of the sequence (e.g., a cloned cDNA) corresponding to the target nucleic acid, to either add or delete nucleotide sequence sufficient to change the size of the amplicon generated when the selected pair of primers is used for amplification. Of course, it should be clear that one would not mutate the sequences bound by the selected primer pair. Site-directed mutagenesis can be performed by any of a number of methods well known in the art.

It can be useful to generate sets of three, four or more competitor nucleic acids. Having additional competitors can either expand or more narrowly define the range of quantitative determination within a given assay. That is, when first and second competitors are used at, for example, a range of concentrations between 10 and 10,000 molecules in a reaction, concentrations of target nucleic acid between 10 and 10,000 molecules in a given volume of the original sample can be determined from the standard curve generated by the competitors. While this determination can be quite accurate, a narrower range of competitor concentrations, e.g., 10 to 500 or 1,000 molecules can increase the accuracy. Similarly, where a first estimate is to be made, the range can be broader, e.g, 10 to 50,000 molecules, with later reactions run at narrower concentrations if desired to more accurately determine the target nucleic acid concentration. It can be advantageous to include three, four or more competitor nucleic acids for a given target nucleic acid at different concentrations in a given reaction. One of skill in the art will recognize that as the concentration of competitors goes up, there may need to be an adjustment in the amount of amplification primers or other parameters for the amplification reaction.

Once a pair of amplification primers is selected and a set of competitor nucleic acids is generated, target nucleic acids in a sample can be quantitated by combining a test nucleic acid sample with the set of at least two competitor nucleic acid molecules, reverse transcribing the target and competitor nucleic acids and amplifying the target and competitor sequences using the pair of amplification primers. In an alternative approach, competitor nucleic acids can be added to a sample prior to extraction of nucleic acid from the test sample. In this instance, target and competitor nucleic acids will be co-isolated.

In order to be most accurate, the competitors should be added to the sample such that at least one is added at a known concentration below that of the target nucleic acid and at least one is added at a known concentration above that of the target nucleic acid. The known concentrations of competitor nucleic acids should differ by at least an order of magnitude (i.e., 10-fold), but can advantageously differ by several orders of magnitude, e.g., at 100-fold, 1,000 fold or more. If the amount of target nucleic acid expected is completely unknown, it can be advantageous to perform one or more preliminary experiments using different ranges of competitors, in order to identify an anticipated range of concentrations for the given target. Alternatively, one or another of a number of less accurate quantitative amplification approaches can be employed to garner a rough estimate of the concentration to expect. Such methods are known in the art and use, for example, titration in a series of parallel reactions against a single reference template.

Reverse transcription is used when the target nucleic acid is an RNA. Reverse transcription is well known in the art and can be performed by an enzyme separate from that used for amplification (e.g., where a reverse transcriptase such as MMLV reverse transcriptase is used) or by the same enzyme (e.g., Tth polymerase or another polymerase known in the art to possess both RNA template-dependent and DNA template-dependent primer extension abilities).

Similarly, DNA amplification is well known in the art. The methods described herein lend themselves well to standard PCR in which a pair of selected primers flanking a target sequence directs the template-dependent synthesis of copied DNA. This does not, however, exclude other methods (e.g., ligase-mediated amplification or other, isothermal, amplification methods, e.g., Self-Sustained Sequence Replication (3SR), Gingeras et al., 1990, Annales de Biologie Clinique, 48(7): 498-501; Guatelli et al., 1990, Proc. Natl. Acad. Sci. U.S.A., 87: 1874; see below) that can be adapted to the approach described herein. A key element in any such alternative approach remains achieving similar efficiency of the amplification from a target RNA and a set of at least two competitor nucleic acids.

3SR is an outgrowth of the transcription-based amplification system (TAS), which capitalizes on the high promoter sequence specificity and reiterative properties of bacteriophage DNA-dependent RNA polymerases to decrease the number of amplification cycles necessary to achieve high amplification levels (Kwoh et al., 1989, Proc. Natl. Acad. Sci. U.S.A., 83: 1173-1177).

In 3SR, each priming oligonucleotide contains a bacteriophage RNA polymerase binding sequence and the preferred transcriptional initiation sequence, e.g., the T7 RNA polymerase binding sequence (TAATACGACTCACTATA; SEQ ID NO: 1) and the preferred T7 polymerase transcriptional initiation site. The remaining sequence of each primer is complementary to the target sequence on the molecule to be amplified.

Exemplary 3SR conditions are described herein as follows. The 3SR amplification reaction is carried out in 100 μl and contains the target RNA, 40 mM Tris-HCl, ph 8.1, 20 mM MgCl2, 2 mM spermidine-HCl, 5 mM dithiothreitol, 80 μg/ml BSA, 1 mM dATP, 1 mM dGTP, 1 mM dTTP, 4 mMATP, 4 mM CTP, 1 mM GTP, 4 mM dTTP, 4 mM ATP, 4 mM CTP, 4 mM GTP, 4 mMUTP, and a suitable amount of oligonucleotide primer (250 ng of a 57-mer; this amount is scaled up or down, proportionally, depending upon the length of the primer sequence). Three to six attomoles of the nucleic acid target for the 3SR reactions is used. As a control for background, a 3SR reaction without any target is run in parallel. The reaction mixture is heated to 100° C. for 1 minute, and then rapidly chilled to 42° C. After 1 minute, 10 units (usually in a volume of approximately 2 μl) of reverse transcriptase, (e.g. avian myoblastosis virus reverse transcriptase, AMV-RT; Life Technologies/Gibco-BRL) is added. The reaction is incubated for 10 minutes, at 42° C. and then heated to 100° C. for 1 minute. (If a 3SR reaction is performed using a single-stranded template, the reaction mixture is heated instead to 65° C. for 1 minute.) Reactions are then cooled to 37° C. for 2 minutes prior to the addition of 4.6 μl of a 3SR enzyme mix, which contains 1.6 μl of AMV-RT at 18.5 units/μl, 1.0 μl T7 RNA polymerase (both e.g. from Stratagene; La Jolla, Calif.) at 100 units/μl, and 2.0 μl E. Coli RNase H at 4 units/μl (e.g. from Gibco/Life Technologies; Gaithersburg, Md.). It is well within the knowledge of one of skill in the art to adjust enzyme volumes as needed to account for variations in the specific activities of enzymes drawn from different production lots or supplied by different manufacturers. Variations can also be made to the units of the enzymes as necessary. The reaction is incubated at 37° C. for 1 hour and stopped by freezing.

Where the progress of the amplification is to be monitored by sampling, the sampling can be performed at any stage of the 3SR reaction. Because 3SR proceeds continuously at a single temperature, there are not individual cycles at which aliquots will be withdrawn. Thus, sampling can be performed at set times during the amplification incubation period, for example, every minute, every two minutes, every three minutes, etc. Nucleic acids in the aliquots withdrawn or extruded are then separated and nucleic acids detected, thereby permitting the generation of an amplification profile, from which the abundance of target in the initial sample can be determined.

3SR is also referred to by some as Nucleic Acid Sequence Based Amplification, or NASBA (see for example, Compton, 1991, Nature, 350: 91-92; Kievits et al., 1991, J. Virol Meth. 35: 273-286, each of which is incorporated herein by reference).

Another method of nucleic acid amplification that is of use according to the invention is the DNA ligase amplification reaction (LAR), which has been described as permitting the exponential increase of specific short sequences through the activities of any one of several bacterial DNA ligases (Wu and Wallace, 1989, Genomics, 4: 560; Barany, 1991, Proc. Natl. Acad. Sci. USA 88: 189, each of which is incorporated herein by reference). This technique is based upon the ligation of oligonucleotide probes. The probes are designed to exactly match two adjacent sequences of a specific target nucleic acid. The amplification reaction is repeated in three steps in the presence of excess probe: (1) heat denaturation of double-stranded nucleic acid, (2) annealing of probes to target nucleic acid, and (3) joining of the probes by thermostable DNA ligase. The reaction is generally repeated for 20-30 cycles. The sampling methods disclosed herein permit the generation of a detailed amplification profile. As with any cyclic amplification protocol, where desired, e.g., to establish an amplification profile, sampling can be performed after any cycle, but preferably after each cycle.

Rolling circle amplification (RCA) is an alternative amplification technology that may prove to have as large an impact as PCR. This technique draws on the DNA replication mechanism of some viruses. In RCA, similar to the replication technique used by many viruses, a polymerase enzyme reads off of a single promoter around a circle of DNA—continuously rolling out linear, concatenated copies of the circle. In such linear RCA, the reaction can run for three days, producing millions of copies of the small circle sequence. An exponential variant has been developed in which a second promoter displaces the double strands at each repeat and initiates hyperbranching in the DNA replication, creating as many as $10^{12}$ copies per hour.

Another amplification method that can benefit from the sampling methods disclosed herein is strand-displacement amplification (SDA; Walker et al., 1992, Nucleic Acids Res., 20: 1691-1696; Spargo et al., 1993, Mol. Cellular Probes 7: 395-404, each of which is incorporated herein by reference). SDA uses two types of primers and two enzymes (DNA polymerase and a restriction endonuclease) to exponentially produce single-stranded amplicons asynchronously. A variant of the basic method in which sets of the amplification primers were anchored to distinct zones on a chip reduces primer-primer interactions. This so-called "anchored SDA" approach permits multiplex DNA or RNA amplification without decreasing amplification efficiency (Westin et al., 2000, Nature Biotechnology 18: 199-204, incorporated herein by reference). SDA can benefit from sampling and separation as described herein, as repeated sampling permits the generation of a detailed amplification profile.

Following reverse-transcription and amplification, the methods described herein involve the separation of nucleic acid amplification products by size. Size separation of nucleic acids is well known, e.g., by agarose or polyacrylamide electrophoresis or by column chromatography, including HPLC separation. A preferred approach uses capillary electrophoresis, which is both rapid and accurate, readily achieving separation of molecules differing in size by only one nucleotide. Capillary electrophoresis uses small amounts of sample and is well-adapted for detection by, for example, fluorescence detection. Capillary electrophoresis is well known in the art and is described in further detail herein below.

As discussed above, amplified nucleic acids corresponding to the target nucleic acid and competitor nucleic acids are detected after separation. The detection notes both the position of a given band of nucleic acid of a given size and the abundance of that nucleic acid by, for example, UV absorption or, preferably, fluorescent signal. Fluorescent nucleotides can be incorporated into the amplified nucleic acid by simply adding one or more such nucleotides to the amplification reaction mixture prior to or during amplification. An alternative approach is to fluorescently label one or more amplification primers such that every strand amplified from that primer has at least one fluorescent label associated with it. While the methods described here are fully intended to encompass the use of fluorescently labeled nucleotide analogs for labeling the amplified products, an advantage of labeling one or more amplification primers is that primers for different target nucleic acids can be differentially labeled with different fluorophores, to expand, for example, the scope of multiplexing possible with the methods described herein. With this approach, additional sets of target and competitor amplicons of even similar size can be distinguished in the same reaction.

Following detection of amplified, separated target and competitor molecules, the methods described herein use the amounts of the competitors detected as a standard. Because the original concentrations of the competitors is known, and the signal from the amplified sequences will be proportional to the starting amounts of each sequence, and the efficiency of amplification is similar for each of the target and competitor molecules, the amount of the target nucleic acid in the original sample can be determined from the amount of the competitors. The accuracy of the method is further enhanced when, as is preferred, the competitors, as internal standards, were originally present at concentrations that flank the concentration of the target molecule.

It is noted that amplification approaches such as PCR generally exhibit kinetics such that there is a limited exponential phase of the amplification process in which the amount of amplified template is closely proportional to the amount of original template in the reaction. The exact location of this phase in a given cycling regimen will vary depending upon factors including the target sequence, primer sequences and the initial abundance of the target template. The methods described herein are well adapted to determining exactly when in the cycling regimen a given target sequence was (or is, when cycling and detection are performed simultaneously or at least contemporaneously) being amplified in the exponential phase. Thus, in one aspect, the methods described herein can benefit from repeated sampling during the amplification cycling regimen, coupled with separation and detection of the target and competitor nucleic acids in the withdrawn samples. The detection of, for example, fluorescently labeled target and competitor amplicons at multiple cycles during the amplification permits one to generate a plot (most often plotted automatically) of target and competitor amplicon abundance versus cycle number. This approach accurately identifies the phase for any given target or competitor at which the amplification is proceeding in exponential phase, which in turn permits the identification of the original quantity of the target template. The addition of the internal standards represented by the known concentrations of the longer and shorter competitors further enhances the accuracy of the data that can be obtained in this manner. That is, one not only has the internal standards that provide a curve from which to identify original concentration, but one also has the benefit of knowing at which point in the reaction the correspondence between initial template and amplified product is best.

Sample withdrawal during the amplification cycling regimen can be performed manually, or, preferably automatically, e.g., under robotic control. Automated sampling can enhance the uniformity of the timing of sample withdrawal, and can help to avoid cross-contamination that might occur under manual sampling conditions. Automated sampling and analysis apparatuses (including capillary electrophoresis apparatuses) are described in co-pending U.S. patent application Ser. No. 10/387,286, filed Mar. 12, 2003, the entirety of which is incorporated herein by reference.

In another aspect, the quantitative approach described herein is adapted for multiplexing—the determination of a plurality of target nucleic acids in a given sample in a single reaction. This is preferably achieved by selecting target amplicon and competitor amplicon sizes such that different sets of target and competitor amplicons, distinguishable by amplicon size, are generated for each different target nucleic acid. Alternatively, or in addition, different target amplicons can be differentially detected in the same reaction by using differentially labeled amplification primers specific for different target/competitor amplicon sets. Basic multiplex PCR approaches and the considerations necessary to perform them successfully are known in the art and are readily applied to the methods described herein in which the ability to efficiently separate and detect amplicons of differing sizes from different known targets permits the detection of multiple (e.g., 2, 3, 5, 10, 20, 50 or more) target signals in a single reaction. Multiplex PCR generally requires that interactions between primers specific for different targets be minimized in order to reduce artifacts—that is, one seeks to avoid the ability of any two primers being used in a reaction to hybridize to each other, instead of to their respective target molecules. Commonly available software packages permit the analysis and prediction of primer-primer interactions for a given set of primers.

Primer Design:

The methods described herein rely upon the use of DNA oligonucleotide primers for the amplification of target and competitor sequences. Oligonucleotide primers for use in these methods can be designed according to general guidance well known in the art as described herein, as well as with specific requirements as described herein for each step of the particular methods described.

1. General Strategies for Primer Design

Oligonucleotide primers are 5 to 100 nucleotides in length, preferably from 17 to 45 nucleotides, although primers of different length are of use. Primers for synthesizing cDNAs are preferably 10-45 nucleotides, while primers for amplification are preferably about 17-25 nucleotides. Primers useful in the methods described herein are also designed to have a particular melting temperature (Tm) by the method of melting temperature estimation. Commercial programs, including Oligo™, Primer Design and programs available on the internet, including Primer3 and Oligo Calculator can be used to calculate a Tm of a polynucleotide sequence useful according to the invention. Preferably, the Tm of an amplification primer useful according to the invention, as calculated for example by Oligo Calculator, is preferably between about 45 and 65° C. and more preferably between about 50 and 60° C.

Tm of a polynucleotide affects its hybridization to another polynucleotide (e.g., the annealing of an oligonucleotide primer to a template polynucleotide). In the subject methods, it is preferred that the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., 1984, Polynucleotides Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides. 100% complementarity is preferred for the methods described herein.

Numerous factors influence the efficiency and selectivity of hybridization of the primer to a second polynucleotide molecule. These factors, which include primer length, nucleotide sequence and/or composition, hybridization temperature, buffer composition and potential for steric hindrance in the region to which the primer is required to hybridize, are considered when designing oligonucleotide primers useful in the methods described herein.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer (for example, 1×RT buffer, Stratagene Catalog #600085, 1×Pfu buffer, Stratagene Catalog #200536; or 1× cloned Pfu buffer, Stratagene Catalog #200532, or other buffer suitable for other enzymes used for cDNA synthesis and amplification) under conditions that allow the polynucleotide sequence to hybridize to the oligonucleotide primers (e.g., 95° C. for PCR amplification). Stringent hybridization conditions can vary (for example from salt concentrations of less than about 1M, more usually less than about 500 mM and preferably less than about 200 mM) and hybridization temperatures can range (for example, from as low as 0° C. to greater than 22° C., greater than about 30° C., and (most often) in excess of about 37° C.) depending upon the lengths and/or the polynucleotide composition or the oligonucleotide primers. Longer fragments may require higher hybridization temperatures for specific hybridization. As several factors affect the stringency of hybridization, the combination of parameters is more important than the absolute measure of a single factor.

The design of a primer set useful in the methods described herein can be facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., supra).

2. Oligonucleotide Synthesis

The oligonucleotide primers themselves are synthesized using techniques that are also well known in the art. Methods for preparing oligonucleotides of specific sequence include, for example, cloning and restriction digestion of appropriate sequences and direct chemical synthesis. Once designed, oligonucleotides can also be prepared by a suitable chemical synthesis method, including, for example, the phosphotriester method described by Narang et al., 1979, Methods in Enzymology, 68: 90, the phosphodiester method disclosed by Brown et al., 1979, Methods in Enzymology, 68: 109, the diethylphosphoramidate method disclosed in Beaucage et al., 1981, Tetrahedron Letters, 22: 1859, and the solid support method disclosed in U.S. Pat. No. 4,458,066, or by other chemical methods using either a commercial automated oligonucleotide synthesizer (which is commercially available) or VLSIPS™ technology.

Competitor RNA Design and Synthesis:

Competitor nucleic acids should be amplified by the same primer set selected for a given target RNA and have similar amplification efficiency to the target nucleic acid with the same selected set of primers. The competitor nucleic acids should yield amplification products, with the selected set of primers, that are distinguishable in length from each other and from the amplification product from the target nucleic acid. The resolution of chosen separation techniques will necessarily bear upon the differences in length that are distinguishable. As noted above, differences of as little as one nucleotide are routinely achievable, although even in these instances, it may be useful to have somewhat longer lengths, in order to provide better distinction in signal. A key consideration is having the length difference long enough to be detectable by the selected method, e.g., capillary electrophoresis, but short enough that it does not significantly modify the amplification efficiency relative to that of the target nucleic acid. That is, the amplification efficiency of the longer or shorter competitor nucleic acid must be similar to that of the target nucleic acid.

As discussed above, competitor nucleic acids are characterized by the presence of sequences which permit their amplification by the same pair of oligonucleotide primers selected to amplify a given target nucleic acid. Amplification of the competitor nucleic acid by the same pair of primers as used to amplify the target nucleic acid assures that the annealing efficiency of the primers to both the target and competitor sequences is the same, which is important for assuring similar amplification efficiency of the competitor and target nucleic acids.

To maintain similar amplification efficiency, it is important that competitor nucleic acids (or, more accurately, their amplification products) have similar $T_m$ to the target nucleic acid (or its amplification products). Methods for the estimation of $T_m$ for any given sequence are well known in the art. $T_m$ is similar if, for example, it is within 1-2° C., but preferably within 0.5 to 1° C. or even less difference, relative to the target nucleic acid. It is preferred that competitor and target nucleic acids comprise at least 20 nucleotides or base pairs of identical sequence. This is preferably in addition to common primer binding sequences. The primer-binding sequences of the target and competitor nucleic acids do not need to be identical, but should operate to permit amplification by the same primers. Because differences in primer annealing efficiency affect amplication efficiency, it is most straight-forward to maintain identity in these sequences between target and competitior sequences.

One of the most straightforward ways of generating competitor nucleic acids that will have the necessarily similar amplification efficiency to the target nucleic acid is to modify a cloned cDNA corresponding to the target nucleic acid, by inserting or deleting a short (e.g., a 1-20 nucleotide insertion or deletion e.g., a 5-20 nucleotide or 5-10 nucleotide insertion or deletion) stretch in the target sequence itself (i.e., an internal insertion or deletion). This assures similar characteristics for annealing and amplification efficiency, with the only differences being the internal insertion or deletion. While insertion or deletion of a short contiguous sequence is more easily accomplished, the insertion or deletion encompassed by this embodiment can also include insertion or deletion on non-contiguous nucleotides or base pairs—that is, removal or insertion at more than one location within the target sequence. For shorter target amplicon sequences, e.g., 50 to 75 nucleotides, it is beneficial to keep the difference in length to the shorter end of this spectrum, e.g., 1 to 5 nucleotides, as this represents a smaller change in make-up of the sequence on a percentage basis. For longer target amplicon sequences, the length difference can be longer without having as dramatic an impact on the amplification characteristics of the molecule. Even in the context of longer target amplicon sequences, the insertion or deletion is still preferably 10 nucleotides (or base pairs) or fewer, particularly where the size separation will be performed with a method, e.g., CE, which is capable of resolution on the basis of as little as 1 nucleotide or base pair.

One of skill in the art will understand that one factor affecting amplification efficiency is the presence of repeat stretches of the same nucleotide, e.g., poly A, poly G, etc., which tend to reduce the efficiency of amplification relative to a similar sequence without the repeats. Thus, when considering the sequence to add, or, for that matter, to delete, it is best to add or delete sequence that is approximately balanced in nucleotide composition. The sequence added or deleted can be amino acid coding or non-coding sequence, and can optionally comprise conventional or non-conventional nucleotides, if so desired.

The insertion or deletion of sequence useful in generating a set of competitor nucleic acids is readily achieved using site-directed mutagenesis techniques well known in the art. A number of methods are known in the art that permit the targeted mutation of DNA sequences (see for example, Ausubel et. al. *Short Protocols in Molecular Biology* (1995) 3$^{rd}$ Ed. John Wiley & Sons, Inc.). In addition, there are a number of commercially available kits for site-directed mutagenesis, including both conventional and PCR-based methods. Examples include the GeneMorph Random mutagenesis kit (Stratagene Catalog No. 600550 or 200550), EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

The measurement of amplification efficiency is described herein below.

Once competitor sequences are designed, the competitor nucleic acid for use in the methods described herein can be generated by, for example, chemical synthesis as known in the art, PCR, or, when the competitor nucleic acid is an RNA, by in vitro transcription. The technique of in vitro transcription is well known to those of skill in the art. Briefly, the sequence of interest is linked to a promoter sequence for a prokaryotic polymerase, such as the bacteriophage T7, T3 and Sp6 RNA polymerase promoter, followed by in vitro transcription of the DNA template using the appropriate polymerase. The template can itself be a linear PCR product into which the promoter has been incorporated, for example, by inclusion of the appropriate promoter sequence in one of the PCR amplification primers. Where desired, linkage to two different promoters, one on each end, creates the potential for also generating the complement of the competitor RNA.

Alternatively, a DNA sequence corresponding to a desired competitor RNA can be inserted into a vector containing an Sp6, T3 or T7 promoter. The vector is linearized with an appropriate restriction enzyme that digests the vector at a single site located downstream of the competitor sequence. Following a phenol/chloroform extraction, the DNA is ethanol precipitated, washed in 70% ethanol, dried and resuspended in sterile water. Regardless of the exact form of the promoter/template construct (i.e., linear PCR product or linearized vector construct), the in vitro transcription reaction is performed by incubating the linear DNA with transcription buffer (200 mM Tris-HCl, pH 8.0, 40 mM $MgCl_2$, 10 mM spermidine, 250 NaCl [T7 or T3] or 200 mM Tris-HCl, pH 7.5, 30 mM $MgCl_2$, 10 mM spermidine [Sp6]), dithiothreitol, RNase inhibitors, each of the four ribonucleoside triphosphates, and either Sp6, T7 or T3 RNA polymerase, e.g., for 30 min at 37° C. If it is desired to prepare a labeled polynucleotide comprising RNA, unlabeled UTP can be omitted and labeled UTP can be included in the reaction mixture. Labels can include, for example, fluorescent or radiolabels. The DNA template is then removed by incubation with DNaseI. Phenol extraction can be used to remove the DNAse and polymerase, followed by precipitation and quantitation of the RNA, e.g., by UV absorption and/or by electrophoresis and visualization relative to known standards.

Polymerase Chain Reaction:

PCR provides a well-established method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR is described in Mullis and Faloona, 1987, Methods Enzymol., 155: 335, incorporated herein by reference, as well as in U.S. Pat. Nos. 4,683,202, 4,683,195 and 4,800,159, each of which is also incorporated herein by reference. Reaction conditions for the amplification of a chosen target sequence can be readily selected or determined with a minimum of experimentation by one of ordinary skill in the art. Numerous variations on the basic theme are also known to those of skill in the art.

The length and temperature of each step of a PCR cycle (denaturation, primer annealing, and extension), as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of ordinary skill in the art. An annealing temperature of between 30° C. and 72° C. is most often used. Initial denaturation of the template molecules normally occurs at between 92° C. and 99° C., e.g., for 4 minutes, followed by 10-40 cycles consisting of denaturation (94-99° C. for 15 seconds to 1 minute), annealing (temperature determined as discussed above; 30 seconds to 2 minutes), and extension (72° C. for 30 seconds to 1 minute; this is optimal for Taq polymerase—one of skill in the art will know or can easily determine suitable extension conditions for different thermostable polymerases). Depending upon the intended use of the product, a final extension step is often carried out for a longer time, e.g., 4 minutes at 72° C., and may be followed by an indefinite (0-24 hour) storage at 4° C.

Polymerases:

A wide variety of DNA polymerases can be used in the methods described herein. Suitable DNA polymerases for use in the subject methods may or may not be thermostable, although thermostable polymerases are obviously preferred for the embodiments using thermocycling for amplification. Known conventional DNA polymerases include, for example, *Pyrococcus furiosus* (Pfu) DNA polymerase (Lundberg et al., 1991, Gene, 108: 1, provided by Stratagene), *Pyrococcus woesei* (Pwo) DNA polymerase (Hinnisdaels et al., 1996, Biotechniques, 20: 186-8, provided by Boehringer Mannheim), *Thermus thermophilus* (Tth) DNA polymerase (Myers and Gelfand 1991, Biochemistry 30: 7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent DNA polymerase, Cariello et al., 1991, Polynucleotides Res, 19: 4193, provided by New England Biolabs), Vent exó (New England Biolabs), 9°Nm DNA polymerase (discontinued product from New England Biolabs), *Thermotoga maritima* (Tma) DNA polymerase (Diaz and Sabino, 1998, Braz J. Med. Res, 31: 1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63: 4504), JDF-3 DNA polymerase (from *thermococcus* sp. JDF-3, Patent application WO 0132887), *Pyrococcus* GB-D (PGB-D) DNA polymerase (also referred as Deep-Vent DNA polymerase, Juncosa-Ginesta et al., 1994, Biotechniques, 16: 820, provided by New England Biolabs), UlTma DNA polymerase (from thermophile *Thermotoga maritima*; Diaz and Sabino, 1998, Braz J. Med. Res. 31: 1239; provided by PE Applied Biosystems), Tgo DNA polymerase (from *thermococcus gorgonarius*, provided by Roche Molecular Biochemicals), *E. coli* DNA polymerase I (Lecomte and Doubleday, 1983, Polynucleotides Res. 11: 7505), T7 DNA polymerase (Nordstrom et al., 1981, J. Biol. Chem. 256: 3112), and archaeal DP1/DP2 DNA polymerase II (Cann et al., 1998, Proc. Natl. Acad. Sci. USA 95: 14250-5).

For thermocyclic reactions, the polymerases are preferably thermostable polymerases such as Taq, Deep Vent, Tth, Pfu, Vent, and UlTma, each of which are readily available from commercial sources. Similarly, guidance for the use of each of these enzymes can be readily found in any of a number of protocols found in guides, product literature, the Internet (see, for example, www.alkami.com), and other sources.

For non-thermocyclic reactions, and in certain thermocyclic reactions, the polymerase will often be one of many polymerases commonly used in the field, and commercially available, such as DNA pol 1, Klenow fragment, T7 DNA polymerase, and T4 DNA polymerase. In applications involving transcription, a number of RNA polymerases are also commercially available, such as T7 RNA polymerase and SP6 RNA polymerase. Guidance for the use of such polymerases can readily be found in product literature and in general molecular biology guides such as Sambrook or Ausubel, both supra.

Polymerases can incorporate labeled (e.g., fluorescent) nucleotides or their analogs during synthesis of polynucleotides. See, e.g., Hawkins et al., U.S. Pat. No. 5,525,711, where the use of nucleotide analogs which are incorporatable by Taq is described.

As described above, the amplification reactions required for the methods described herein can generally be carried out using standard reaction conditions and reagents unless otherwise specified. Such reagents and conditions are well known to those of skill in the art, and are described in numerous references and protocols. See, e.g. Innis supra; Sambrook, supra.; Ausubel, et al., eds. (1996) *Current Protocols in Molecular Biology, Current Protocols*, a joint venture between Greene Publishing Associates, Inc. and John Wiley & Sons, Inc. Also, see, Mullis et al., (1987) U.S. Pat. No. 4,683,202, and Arnheim & Levinson (1990) C&EN 6-47, The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem 35: 1826; Landegren et al., (1988) Science 241: 1077-1080; Van Brunt (1990) Biotechnology 8: 291-294; Wu and Wallace, (1989) Gene 4: 560; Barringer et al. (1990) Gene 89: 117, and Sooknanan and Malek (1995) Biotechnology 13: 563-564.

Amplification Efficiency:

As discussed above, the amplification efficiency of the competitor nucleic acid should be similar to that of the target nucleic acid. In one aspect, amplification efficiency is expressed as the fold amplification per PCR cycle, represented as a fraction or percentage relative to perfect doubling. A 100% or 1.0 amplification efficiency would refer to perfect doubling.

One way to monitor amplification efficiency is to measure the threshold cycle number (Ct) at which signal intensity of PCR product reaches a set threshold value (for example 10 standard deviations of background value of signal intensity) for an amplified product. Samples are withdrawn at, for example, each cycle during the amplification regimen and analyzed for the amount of target amplicon. Comparison of Ct for equal starting amounts of two different amplification templates, e.g., a target RNA and a competitor RNA will determine whether the amplification efficiency is similar. To enhance accuracy, the determination can be performed at several different equal starting concentrations of target and competitor RNAs. Amplification efficiency is considered "similar" if the threshold cycle, Ct, is the same for equal starting amounts of each competitor/target set.

Ct is linked to the initial copy number or concentration of starting DNA by a simple mathematical equation:

Log(copy number)=$aC_t+b$, where a and b are constants.

Therefore, by measuring $C_t$ for the fragments of the same gene originating from two different samples, the original concentration of this gene in these samples can be easily evaluated. Alternatively, amplification efficiency is monitored by measuring the amount of amplification product (e.g., by fluorescence intensity or label incorporation) at successive cycles, calculating efficiency using the formula $E=(P_{n+1}-P_n)/(P_n-P_{n-1})$, where P is the amount of amplification product at cycle n.

While the similarity in amplification efficiencies will ultimately be determined empirically, the maintenance of target sequence identity in the competitors, except for an insertion or deletion necessary to generate a detectable difference in length relative to the target, will assist in achieving similar efficiencies.

It is known that the presence of various contaminants in a nucleic acid sample preparation can have an effect on amplification efficiency. An advantage of the methods described herein is that any such contaminant will most likely affect the efficiency of amplification of both the competitor and target amplicons to a similar degree, because each of these amplicons is generated in the same reaction. This will tend to reduce the impact of any such inhibition of efficient amplification.

Preparation of Samples

A target polynucleotide of the present invention may be single- or double-stranded, and it may be DNA (e.g., gDNA or cDNA), RNA, a polynucleotide comprising both deoxyribo- and ribonucleotides, or a polynucleotide comprising deoxyribonucleotides, ribonucleotides, and/or analogs and derivatives thereof. Where one wishes to determine the level of expression of a gene, the target polynucleotide is an RNA molecule, e.g., an mRNA molecule.

Before the amplification reaction, the target polynucleotide may be obtained in suitable quantity and quality for the chosen amplification method to be used. For example, in some instances, the samples contain such a low level of target polynucleotide that it is useful to conduct a pre-amplification reaction to increase the concentration of the target polynucleotide. If samples are to be amplified, amplification is typically conducted using the polymerase chain reaction (PCR) according to known procedures. In some embodiments, it may be preferred to add known quantities of the competitor nucleic acids to a biological sample prior to co-isolation of competitor and test nucleic acids in the sample.

Guidance for the preparation of a sample containing a target polynucleotide can be found in a multitude of sources, including *PCR Protocols, A Guide to Methods and Applications* (Innis et al., supra; Sambrook et al., supra; Ausubel et al., supra). Any such method can be used in methods described herein. Typically, these methods involve cell lysis, followed by purification of polynucleotides by methods such as phenol/chloroform extraction, electrophoresis, and/or chromatography. Often, such methods include a step wherein the polynucleotides are precipitated, e.g. with ethanol, and resuspended in an appropriate buffer for addition to a PCR or similar reaction.

In certain embodiments, two or more target polynucleotides from one or more sample sources are analyzed in a single reaction. In some applications, a single polynucleotide from a multitude of sources may be synthesized to screen for the presence or absence of a particular sequence difference. In other applications, a plurality of polynucleotides may be amplified from a single sample or individual, thereby allowing the assessment of a variety of polynucleotides in a single individual, e.g., to simultaneously screen for a multitude of disease markers in an individual. Any of the above applications can be easily accomplished using the methods described herein.

A reaction mixture may comprise one target polynucleotide, or it may comprise two or more target polynucleotides. The present method allows for simultaneous analysis of two or more polynucleotides obtained from a plurality of samples, i.e., multiplex analysis.

In one aspect of the invention, a nucleic acid sample may be derived from a sample from an animal suffering from an infectious disease (e.g., a disease of bacterial, fungal, viral or parasitic origin) and another sample of may be from an animal not suffering from an infectious disease. In another aspect, a nucleic acid sample may be may be derived from an animal suffering from cancer and another may be derived from an animal not suffering from cancer. In another aspect, one an a nucleic acid sample may be may be obtained from a cancerous animal tissue and another may be obtained from a noncancerous animal tissue, which tissues may both be obtained from the same animal. In another aspect, a nucleic acid sample may be may be from an animal suffering from a genetic disease and another sample may be from an animal not suffering from a genetic disease. In another aspect, a nucleic acid sample may be may be obtained from a pathogenic microorganism and another library or sample may be obtained from a non-pathogenic microorganism. In another aspect, a nucleic acid sample may be derived from an organism expressing an enzyme, and another may be derived from an organism not expressing an enzyme. Other suitable sources of a nucleic acid sample will be apparent to one of ordinary skill in the art.

Once the starting cells, tissues, organs or other samples are obtained, nucleic acids (including RNA and/or DNA) can be prepared therefrom by methods that are well-known in the art.

RNA can be purified, for example, from tissues according to the following method. Following removal of the tissue of interest, pieces of tissue of $\leq 2$ g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-HCl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 120 C. The resulting supernatant is incubated for 2 min at 650 C in the presence of 0.1 volume of 20% Sarkosyl, layered over 9 ml of a 5.7M CsCl solution (0.1 g CsCl/ml), and separated by centrifugation overnight at 113,000×g at 220 C. After careful removal of the supernatant, the tube is inverted and drained. The bottom of the tube (containing the RNA pellet) is placed in a 50 ml plastic tube and incubated overnight (or longer) at 40 C in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, Biochemistry, 18: 5294).

Alternatively, RNA can be isolated from tissues according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4□C after all components have been added. The sample is separated by centrifugation for 20 min at 10,000×g, 4□C, precipitated by the addition of 1 ml of 100% isopropanol, incubated for 30 minutes at −20□C and pelleted by centrifugation for 10 minutes at 10,000×g, 4□C. The resulting RNA pellet is dissolved in 0.3 ml denaturing solution, transferred to a microfuge tube, precipitated by the addition of 0.3 ml of 100% isopropanol for 30 minutes at −20□C, and centrifuged for 10 minutes at 10,000×g at 4□C. The RNA pellet is washed in 70% ethanol, dried, and resuspended in 100-200 µl DEPC-treated water or DEPC-treated 0.5% SDS (Chomczynski and Sacchi, 1987, Anal. Biochem., 162: 156).

Kits and reagents for isolating total RNAs are commercially available from various companies, for example, RNA isolation kit (Stratagene, La Lola, Calif., Cat # 200345); PicoPure™ RNA Isolation Kit (Arcturus, Mountain View, Calif., Cat # KIT0202); RNeasy Protect Mini, Midi, and Maxi Kits (Qiagen, Cat # 74124).

In some embodiments, total RNAs are used in the subject method for subsequent analysis, e.g., for reverse transcription. In other embodiments, mRNAs are isolated from the total RNAs or directly from the samples to use for reverse transcription. Kits and reagents for isolating mRNAs are commercially available from, e.g., Oligotex mRNA Kits (Qiagen, Cat # 70022).

Labeled Nucleotides

The methods described herein can benefit from the use of labels including, e.g., fluorescent labels. In one aspect, the fluorescent label can be a label or dye that intercalates into or otherwise associates with amplified (usually double-stranded) nucleic acid molecules to give a signal. One stain useful in such embodiments is SYBR Green (e.g., SYBR Green I or II, commercially available from Molecular Probes Inc., Eugene, Oreg.). Others known to those of skill in the art can also be employed in the methods described herein. An advantage of this approach is reduced cost relative to the use of, for example, labeled nucleotides. Nonetheless, it may also be preferred that the label will be incorporated by attachment to a labeled nucleotide or nucleotide analog that is a substrate for the polymerizing enzyme. Label can alternatively be attached to an amplification primer. As taught above, a labeled nucleotide can be a fluorescent dye-linked nucleotide, or it can be an intrinsically fluorescent nucleotide. In one embodiment of the methods described herein, a conventional deoxynucleotide linked to a fluorescent dye is used. Non-limiting examples of some useful labeled nucleotide are listed in Table 1.

TABLE 1

| Examples of labeled nucleotides | |
| --- | --- |
| Fluorescein Labeled | Fluorophore Labeled |
| Fluorescein - 12 - dCTP | Eosin - 6 - dCTP |
| Fluorescein - 12 - dUTP | Coumarin - 5 - ddUTP |

TABLE 1-continued

| Examples of labeled nucleotides | |
| --- | --- |
| Fluorescein - 12 - dATP | Tetramethylrhodamine - 6 - dUTP |
| Fluorescein - 12 - dGTP | Texas Red - 5 - dATP |
| Fluorescein - N6 - dATP | LISSAMINE ™ - rhodamine - 5 - dGTP |
| FAM Labeled | TAMRA Labeled |
| FAM - dUTP | TAMRA - dUTP |
| FAM - dCTP | TAMRA - dCTP |
| FAM - dATP | TAMRA - dATP |
| FAM - dGTP | TAMRA - dGTP |
| ROX Labeled | JOE Labeled |
| ROX - dUTP | JOE - dUTP |
| ROX - dCTP | JOE - dCTP |
| ROX - dATP | JOE - dATP |
| ROX - dGTP | JOE - dGTP |
| R6G Labeled | R110 Labeled |
| R6G - dUTP | R110 - dUTP |
| R6G - dCTP | R110 - dCTP |
| R6G - dATP | R110 - dATP |
| R6G - dGTP | R110 - dGTP |
| BIOTIN Labeled | DNP Labeled |
| Biotin - N6 - dATP | DNP - N6 - dATP |

Fluorescent dye-labeled nucleotide can be purchased from commercial sources. Labeled polynucleotides nucleotide can also be prepared by any of a number of approaches known in the art.

Fluorescent dyes useful as detectable labels are well known to those skilled in the art and numerous examples can be found in the *Handbook of Fluoresdent Probes and Research Chemicals* 6th Edition, Richard Haugland, Molecular Probes, Inc., 1996 (ISBN 0-9652240-0-7).

Preferably, fluorescent dyes are selected for compatibility with detection on an automated capillary electrophoresis apparatus and thus should be spectrally resolvable and not significantly interfere with electrophoretic analysis. Examples of suitable fluorescent dyes for use as detectable labels can be found in among other places, U.S. Pat. Nos. 5,750,409; 5,366,860; 5,231,191; 5,840,999; 5,847,162; 4,439,356; 4,481,136; 5,188,934; 5,654,442; 5,840,999; 5,750,409; 5,066,580; 5,750,409; 5,366,860; 5,231,191; 5,840,999; 5,847,162; 5,486,616; 5,569,587; 5,569,766; 5,627;027; 5,321,130; 5,410,030; 5,436,134; 5,534,416; 5,582,977; 5,658,751; 5,656,449; 5,863,753; PCT Publications WO 97/36960; 99/27020; 99/16832; European Patent EP 0 050 684; Sauer et al, 1995, J. Fluorescence 5: 247-261; Lee et al., 1992, Nucl. Acids Res. 20: 2471-2483; and Tu et al., 1998, Nucl. Acids Res. 26: 2797-2802, all of which are incorporated herein in their entireties.

Nucleotide can be modified to include functional groups, such as primary and secondary amines, hydroxyl, nitro and carbonyl groups, for fluorescent dye linkage (see Table 2).

TABLE 2

| Functional Group | Reaction | Product |
| --- | --- | --- |
| Amine | dye - isothiocyanates | Thiourea |
| Amine | dye - succinimidyl ester | Carboxamide |
| Amine | dye - sulfonyl chloride | Sulphonamide |
| Amine | dye - aldehyde | Alkylamine |
| Ketone | dye - hydrazides | Hydrazones |

TABLE 2-continued

| Functional Group | Reaction | Product |
| --- | --- | --- |
| Ketone | dye - semicarbazides | Hydrazones |
| Ketone | dye - carbohydrazides | Hydrazones |
| Ketone | dye - amines | Alkylamine |
| Aldehyde | dye - hydrazides | Hydrazones |
| Aldehyde | dye - semicarbazides | Hydrazones |
| Aldehyde | dye - carbohydrazides | Hydrazones |
| Aldehyde | dye - amines | Alkylamine |
| Dehydrobutyrine | dye - sulphydryl | Methyl lanthionine |
| Dehydroalanine | dye - sulphydryl | Lanthionine |

Useful fluorophores include, but are not limited to: Texas Red™ (TR), Lissamine™ rhodamine B, Oregon Green™ 488 (2',7'-difluorofluorescein), carboxyrhodol and carboxyrhodamine, Oregon Green™ 500, 6-JOE (6-carboxy-4',5'-dichloro-2',7'-dimethyoxyfluorescein), eosin F3S (6-carobxymethylthio-2',4', 5',7'-tetrabromo-trifluorofluorescein), Cascade Blue™ (CB), aminomethylcoumarin (AMC), pyrenes, dansyl chloride (5-dimethylaminonaphthalene-1-sulfonyl chloride) and other napththalenes, PyMPO, ITC (1-(3-isothiocyanatophenyl)-4-(5-(4-methoxyphenyl)oxazol-2-yl)pyridinium bromide), coumarin, fluorescein, tetrachlorofluorescein, hexachlorofluorescein, Lucifer yellow, rhodamine, BODIPY, tetramethylrhodamine, Cy3, Cy5, Cy7, eosine, and ROX. Combination fluorophores such as fluorescein-rhodamine dimers, described, for example, by Lee et al. (1997), Polynucleotides Research 25:2816, are also suitable. Fluorophores may be chosen to absorb and emit in the visible spectrum or outside the visible spectrum, such as in the ultraviolet or infrared ranges. Suitable fluorescent dye labels are commercially available from Molecular Probes, Inc., Eugene, Oreg., US and Research Organics, Inc., Cleveland, Ohio, US, among other sources, and can be found in the *Handbook of Fluoresdent Probes and Research Chemicals* 6th Edition, Richard Haugland, Molecular Probes, Inc., 1996 (ISBN 0-9652240-O-7).

Figure 1:
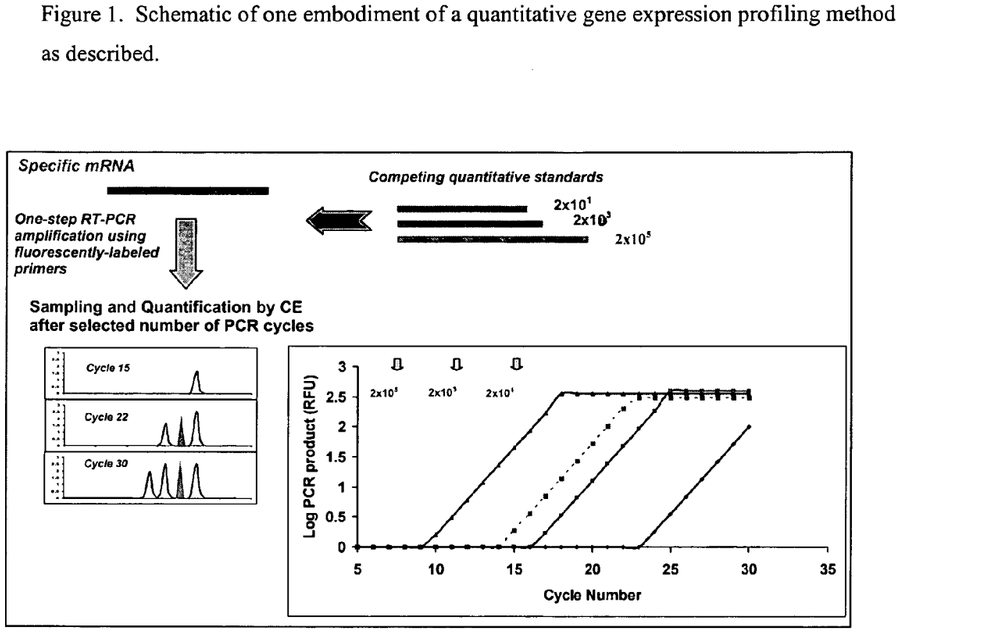
FIG. 1 shows a schematic of one embodiment of a quantitative nucleic acid measurement as described herein.

A labeled nucleotide useful in the methods described herein includes an intrinsically fluorescent nucleotide known in the art, e.g., the novel fluorescent nucleoside analogs as described in U.S. Pat. No. 6,268,132B1 (the entirety is hereby incorporated by reference). The fluorescent analogs of the U.S. Pat. No. 6,268,132B1 are of three general types: (A) C-nucleoside analogs; (B) N-nucleoside analogs; and (C) N-azanucleotide and N-deazanucleotide analogs. All of these compounds have three features in common: 1) they are structural analogs of the common nucleosides capable of replacing naturally occurring nucleosides in enzymatic or chemical synthesis of oligonucleotides; 2) they are naturally fluorescent when excited by light of the appropriate wavelength(s) and do not require additional chemical or enzymatic processes for their detection; and 3) they are spectrally distinct from the nucleosides commonly encountered in naturally occurring DNA. At least 125 specific compounds have been identified in U.S. Pat. No. 6,268,132B1. These compounds, which have been characterized according to their class, structure, chemical name, absorbance spectra, emission spectra, and method of synthesis, are tabulated as shown in FIGS. 21A-21F-1 of the U.S. Pat. No. 6,268,132B1.

The labeled nucleotide as described herein also includes, but is not limited to, fluorescent N-nucleosides and fluorescent structural analogs. Formycin A (generally referred to as Formycin), the prototypical fluorescent nucleoside analog, was originally isolated as an antitumor antibiotic from the culture filtrates of *Nocardia interforma* (Hori et al. [1966] J. Antibiotics, Ser. A 17:96-99) and its structure identified as 7-amino-3-b-D-ribafuranosyl (1H-pyrazolo-[4,3d]pyrimidine)) (FIGS. 5 and 6). This antibiotic, which has also been isolated from culture broths of *Streptomyces lavendulae* (Aizawa et al. [1965] Agr. Biol. Chem. 29:375-376), and *Streptomyces gummaensis* (Japanese Patent No. 10,928, issued in 1967 to Nippon Kayaku Co., Ltd.), is one of numerous microbial C-ribonucleoside analogs of the N-nucleosides commonly found in RNA from all sources. The other naturally-occurring C-ribonucleosides which have been isolated from microorganisms (FIG. 4) include formycin B (Koyama et al. [1966] Tetrahedron Lett. 597-602; Aizawa et al., supra; Umezawa et al. [1965] Antibiotics Ser. A 18:178-181), oxoformycin B (Ishizuka et al. [1968] J. Antibiotics 21:1-4; Sawa et al. [1968] Antibiotics 21:334-339), pseudouridine (Uematsu and Suahdolnik [1972] Biochemistry 11:4669-4674), showdomycin (Darnall et al. [1967] PNAS 57:548-553), pyrazomycin (Sweeny et al. [1973] Cancer Res. 33:2619-2623), and minimycin (Kusakabe et al. [1972] J. Antibiotics 25:44-47). Formycin, formycin B, and oxoformycin B are pyrazolopyrimidinenucleosides and are structural analogs of adenosine, inosine, and hypoxanthine, respectively; a pyrazopyrimidine structural analog of guanosine obtained from natural sources has not been reported in the literature. A thorough review of the biosynthesis of these compounds is available in Ochi et al. (1974) J. Antibiotics xxiv:909-916. The entirety of each reference is here by incorporated by reference.

Separation and Detection of Amplified Products:

Methods for detecting the presence or amount of polynucleotides are well known in the art and any of them can be used in the methods described herein so long as they are capable of separating individual polynucleotides by at least the difference in length between competitor and target amplicons. The separation technique used should permit resolution of sequences from 25 to 1000 nucleotides or base pair, long and have a resolution of 10 nucleotides or base pairs or better. The separation can be performed under denaturing or under non-denaturing or native conditions—i.e., separation can be performed on single- or double-stranded nucleic acids. It is preferred that the separation and detection permits detection of length differences as small as one nucleotide. It is further preferred that the separation and detection can be done in a high-throughput format that permits real time or contemporaneous determination of amplicon abundance in a plurality of reaction aliquots taken during the cycling reaction. Useful methods for the separation and analysis of the amplified products include, but are not limited to, electrophoresis (e.g., capillary electrophoresis (CE)), chromatography (dHPLC), and mass spectrometry.

In one embodiment, CE is a preferred separation means because it provides exceptional separation of the polynucleotides in the range of at least 10-1,000 base pairs with a resolution of a single base pair. CE can be performed by methods well known in the art, for example, as disclosed in U.S. Pat. Nos. 6,217,731; 6,001,230; and 5,963,456, which are incorporated herein by reference. High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3100 genetic analyzer (Applied Biosystems, Foster City, Calif.). Near the end of the CE column, in these devices the amplified DNA fragments pass a fluorescent detector which measures signals of fluorescent labels. These apparatuses provide automated high throughput for the detection of fluorescence-labeled PCR products.

The employment of CE in the methods described herein permits higher productivity compared to conventional slab gel electrophoresis. The separation speed is limited in slab gel electrophoresis because of the heat produced when the high electric field is applied to the gel. Since heat elimination is very rapid from the large surface area of a capillary, a higher electric field can be applied in capillary electrophoresis, thus accelerating the separation process. By using a capillary gel, the separation speed is increased about 10 fold over conventional slab-gel systems.

With CE, one can also analyze multiple samples at the same time, which is essential for high-throughput. This is achieved, for example, by employing multi-capillary systems. In some instances, the detection of fluorescence from DNA bases may be complicated by the scattering of light from the porous matrix and capillary walls. However, a confocal fluorescence scanner can be used to avoid problems due to light scattering (Quesada et al., 1991, Biotechniques 10: 616-25).

In one embodiment, the methods described herein measure the amount (i.e., copy number) of a particular target nucleic acid (e.g., DNA or RNA) contained in the sample used as template for amplification.

In another embodiment, differences in gene expression, rather than the exact copy numbers of the target polynucleotide contained in the sample are measured. The detected signal strength following size separation can be recorded for each of the at least two competitors and the target RNA in two separate samples and used to determine the relative ratio of the target polynucleotide from two samples. A threshold cycle number (Ct) is calculated as a cycle number at which signal intensity of PCR product will reach a set threshold value (for example 10 standard deviations of background value of signal intensity) for an amplified product. Operational differential expression of a particular target is determined as a difference in threshold cycle number (Ct) for this target in two (or more) samples, of more than one cycle in value. In addition to the quantitation achieved by reference to the signals from the at least two competitor RNAs in such an embodiment, the threshold cycle number for a given target in a given reaction can be further used to derive copy number for the target polynucleotide and to measure the difference in the expression by a ratio of copy numbers for the target in two or more samples.

EXAMPLES

Various embodiments of the invention are exemplified in the following non-limiting examples.

1) Quantitative Measurement of a Target RNA.

To determine quantity of target RNA "X", to the sample of RNA containing specific RNA "X" two quantitative competitive standards A and B are added in the quantities of 20 copies of standard A and 2000 copies of standard B.

Quantitative competitive standards A and B are designed in to be co-amplified with target sequence X using the same oligonucleotide primers, and to possess similar (preferably the same) amplification efficiency as target RNA X, and to produce amplified products that differ in size from amplified target RNA X and from each other. For example, target sequence will be amplified in RT-PCR reaction to produce a DNA fragment of 150 bases, standard A will be amplified to produce a fragment of 140 bases, and standard B will be amplified to produce a fragment of 130 bases; sequences of amplified products will be essentially identical with exception of absence of 10 bases in sequence A and the presence of an additional 10 bases in sequence B when compared to the sequence X.

Amplification of target gene and quantitative standards is conducted by RT-PCR as follows:

a) Reverse transcriptase and RT primer are added to RNA to perform reverse transcription (RT) under standard conditions. The RT primer is preferably designed to prime DNA synthesis upstream of the sequence which will be used in PCR amplification. In this approach, following RT, DNA polymerase and a pair of PCR primers are added to conduct PCR amplification under standard conditions.

b) Alternatively, reverse transcriptase, PCR primers and DNA polymerase are added to conduct one-step RT-PCR amplification.

Following RT and PCR, separation of amplified PCR products is performed by CE.

In one of the simplest methods, the signal measured for DNA peaks at 140 and 130 bases (corresponding to standards A and B) will be used to create a calibration corresponding to the starting amounts of 20 and 2000 copies of the standards. The signal generated by unknown amount of target sequence X will be measured at the peak of 150 bases and normalized to the measured signals and starting amounts of standards A and B. Results are shown schematically, for example, in FIG. 1.

2) Quantitative Measurement of a Target RNA.

To extend the calibrated concentration range (to cover possible high concentrations of target X) additional standard C (producing amplified product of 160 bases) can be added at 200000 copies.

The amplification and separation procedure will be conducted as in Example 1 with one modification.

Since the dynamic range of detection of most current CE systems is in the range of 100-1000×, it may not be possible to observe signals from low copies (e.g. 20) and high copies (e.g. 200000) on the same electrophoregram. To overcome this limitation, the amplification reaction will be sampled for CE separation at multiple cycles:

For example: at cycle 15, where signal from target could be normalized to the amplified high copy standard C; at cycle 22 where signal from target could be normalized to the amplified medium copy standard B; at cycle 30 where signal from target could be normalized to the amplified low copy standard A.

3) Multiplex Measurement of Target RNAs.

Multiplex detection of at least two genes X and Y is performed where the reaction is supplemented with standards A and B for target X and standards E and F for target Y, and two separate primer pairs for amplification of targets X and Y correspondingly. Amplification products generated from standards E and F and target Y differ in size from amplification products generated from each of target X and standards A and B.

The assay can be conducted using the procedure from Example 1 or 2, with CE size separation providing discrimination between the amplification products of.

The present invention is not to be limited in scope by the exemplified embodiments which are intended as illustrations of single aspects of the invention. Various modifications of the invention in addition to those described herein will become apparent to those skilled in the art from the foregoing description and accompanying figures. Such modifications are intended to fall within the scope of the appended claims. All publications cited herein are incorporated by reference in their entirety.

The invention claimed is:

1. A method of determining the level of a target nucleic acid in a nucleic acid sample, the method comprising:
   a) for a given target nucleic acid, selecting a pair of first and second amplification primers that will generate a target amplicon of a first known length when said target nucleic acid is subjected to amplification using said pair of primers;
   b) providing at least two nucleic acid competitor molecules:
      i) a first competitor nucleic acid molecule comprising said target nucleic acid sequence plus or minus an internal insertion or deletion of known length, wherein said first nucleic acid competitor is a substrate for amplification by said pair of first and second amplification primers, such amplification generating an amplicon of a second known length that is longer or shorter than said target amplicon by the length of said internal insertion or deletion;
      ii) a second nucleic acid competitor molecule comprising said target nucleic acid sequence plus or minus an internal insertion or deletion of known length, wherein said second nucleic acid competitor is a substrate for amplification by said pair of first and second amplification primers, such amplification generating an amplicon of a third known length, different from said second known length, that is longer or shorter than said target amplicon by the length of said internal insertion or deletion;
      wherein the amplification of said target nucleic acid and said first and second nucleic acid competitor molecules proceeds with similar efficiency;
   c) combining a test nucleic acid sample with said first and second nucleic acid competitor molecules, wherein the respective competitors are added at first and second known concentrations, said concentrations being different by at least one order of magnitude;
   d) performing reverse-transcription and target sequence amplification on the combined nucleic acid sample of step (c) using said pair of first and second amplification primers;
   e) separating the products of amplification step (d); and
   f) detecting the amounts of the target amplicon of said first known length, the competitor amplicon of said second known length and the competitor amplicon of said third known length, wherein when the amount of one said competitor amplicon is greater than the amount of said target amplicon and the amount of the other said competitor amplicon is less than the amount of said target amplicon, the concentration of said target nucleic acid in said sample is determined.

2. The method of claim 1 wherein the amplicons generated by said first and second competitor nucleic acids are shorter than the amplicon generated from said target nucleic acid, each by the length of an internal deletion.

3. The method of claim 1 wherein the amplicons generated by said first and second competitor nucleic acids are longer than the amplicon generated from said target nucleic acid, each by the length of an internal insertion.

4. The method of claim 1 wherein the amplicon generated by said first competitor nucleic acid is longer than the amplicon generated by said target nucleic acid by the length of an internal insertion, and wherein the amplicon generated by said second competitor nucleic acid is shorter than the amplicon generated by said target nucleic acid by the length of an internal deletion.

5. The method of claim 1 wherein said target nucleic acid is a DNA.

6. The method of claim 5 wherein said competitor nucleic acids are DNAs.

7. The method of claim 1 wherein said target nucleic acid is an RNA, and wherein said method comprises before step (d), of reverse-transcribing said target nucleic acid.

8. The method of claim 7 wherein said competitior nucleic acids are RNAs.

9. The method of claim 7 wherein said method measures gene expression of said target RNA.

10. The method of claim 1 wherein said competitor nucleic acids are added to a test sample prior to preparation of nucleic acid from said test ample.

11. The method of claim 1 wherein said separating of step (e) is performed by capillary electrophoresis.

12. The method of claim 1 wherein said step of detecting comprises detection of fluorescent label incorporated into said amplicons during amplification.

13. The method of claim 1 wherein said step of detecting comprises detection of a fluorescent dye that binds double-stranded amplification products.

14. The method of claim 13 wherein said fluorescent dye comprises a SYBR GREEN dye.

15. The method of claim 1 wherein said concentrations of said first and second competitor nucleic acids differ by at least two orders of magnitude.

16. The method of claim 1 wherein said concentrations of said first and second competitor nucleic acids differ by at least three orders of magnitude.

17. The method of claim 1 wherein said amplification is performed in the presence of a fluorescently-labeled nucleotide, such that amplification products are fluorescently labeled.

18. The method of claim 1 wherein a plurality of aliquots of the amplification reaction of step (d) are taken during the amplification regimen, wherein said aliquots, upon separation and detection of nucleic acid permit the generation of an amplification profile for each of said competitor and target nucleic acids.

19. The method of claim 1 wherein at least one additional competitor nucleic acid is combined with said test nucleic acid sample in step (c), wherein said competitor nucleic acid is chosen such that it will generate an amplicon of a length distinguishable from other amplicons generated in said amplification of step (d) and will be amplified by said first and second amplification primers with similar efficiency to the amplification of the other amplicons generated in said amplification step.

20. The method of claim 19 wherein said additional competitor nucleic acid is added to said test nucleic acid sample at a known concentration that differs from the concentration of said first or second competitor nucleic acids by at least one order of magnitude.

21. The method of claim 1 wherein a second set of amplification primers specific for a second target nucleic acid and corresponding competitor nucleic acids of differing lengths and in known concentrations are added, such that at least two target nucleic acids are quantitated in the same reaction by said amplification and detection steps.

22. The method of claim 21 wherein the target nucleic acid and second target nucleic acid are RNAs and wherein said method measures gene expression of said target RNAs.

23. The method of claim 1 wherein said separating step is performed on a sample taken after completion of said amplification.

24. The method of claim 1 wherein said separating step comprises separation of nucleic acids in a plurality of samples removed from said amplification reaction during the course of said amplification reaction.

25. The method of claim 24 further comprising generating a profile of said amplification reaction based on detection of said target amplicon during said amplification reaction.

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Bacteriophage T7

<400> SEQUENCE: 1
taatacgact cactata                                                17